United States Patent [19]

Manneth et al.

[11] Patent Number: 5,998,423

[45] Date of Patent: Dec. 7, 1999

[54] METHODS FOR MODULATING MELANIN PRODUCTION

[75] Inventors: Victor Manneth, Sunnyvale; Rajesh Patel, Redwood City, both of Calif.

[73] Assignee: Therasys, Inc., Redwood City, Calif.

[21] Appl. No.: 08/940,338

[22] Filed: Sep. 30, 1997

Related U.S. Application Data

[60] Provisional application No. 60/027,944, Oct. 8, 1996.

[51] Int. Cl.⁶ .......................... A61K 31/505; A61K 31/52
[52] U.S. Cl. ............................ 514/260; 514/261; 514/263
[58] Field of Search ..................................... 514/261, 263, 514/260

[56] References Cited

U.S. PATENT DOCUMENTS

| | | | |
|---|---|---|---|
| 4,845,081 | 7/1989 | Sloan | 514/232.2 |
| 4,975,433 | 12/1990 | Sloan | 514/274 |
| 5,470,579 | 11/1995 | Bonte et al. | 424/450 |
| 5,540,914 | 7/1996 | Fuller | 424/59 |

*Primary Examiner*—Kimberly Jordan
*Attorney, Agent, or Firm*—Gary Cary Ware & Freidenrich LLP

[57] ABSTRACT

Compositions and methods for the modulation of melanin production are provided in which the active component is an adenosine receptor antagonist or agonist.

20 Claims, 5 Drawing Sheets

N6-Substituted-9-Methyladenines
e.g., R = cytopentyl, cyclohexyl
or norbornyl Triazoloquinoxalines
e.g. CP 68247

Pyrrolo [2,3-d] pyrimidines
e.g. ADPEP

Xanthines
e.g. $R^1$ = methyl, ethyl, propyl
$R^2$ = methyl, ethyl, propyl or butyl
$R^3$ = cycloalkyl, or phenyl

*FIG. 1*

Imidazo [4,5-b] pyridines from U.S. Patent No. 4,977,144

Adenine derivatives from U.S. Patent No. 4,954,504

FIG. 2

$R_1$ = H, Cl, $NH_2$ $R_2$ = cyclopentyl, cyclohexyl, norbornyl, hydroxypropyl, phenyl R' = –H, –CO$(CH_2)_{16}CH_3$ or

R-PIA

Others are CPA, CHA and CCPA

FIG. 3

CGS 15943
[1,2,4] Triazolo [1,5–c] quinazolines

CP 66713
[1,2,4] Triazolo [4,3–a] quinoxalines

HTQZ
thiazolo [2,3–b] quinazolines

METHODS FOR MODULATING MELANIN PRODUCTION

This application claims the benefit of U.S. Provisional Application No. 60/027,944, filed Oct. 08, 1996, the disclosure of which is incorporated by reference.

FIELD OF THE INVENTION

The present invention relates to the use of polycyclic nitrogen heterocycles in topical creams and lotions for modulating melanin production in the skin and hair which is useful in enhancing the tanning process and providing protection for the skin against ultraviolet radiation.

BACKGROUND OF THE INVENTION

The tanning response is characterized clinically by the formation of brown color in the skin that is exposed to ultraviolet radiation and histologically by an increase in the epidermal melanin content. This increase in pigmentation is the outcome of two main events: the synthesis of melanin by melanocytes and the donation of melanin in melanosomes to the surrounding keratinocytes. In mammalian cells the rate of melanin production is determined by the intracellular enzyme Tyrosinase and two related proteins TRP-1 and TRP-2 (Dopachrome tautomerase). Tyrosinase is a copper containing oxidase that catalyzes three different reactions in the melanogenesis pathway. The first two reactions result in the conversion of tyrosine to dopa and in the subsequent conversion of dopa to dopaquinone. The third reaction occurs at the distal step in the pathway, in which 5,6-dihydroxyindole is oxidized to indolequinone. An increase in tyrosinase activity provides an increase in tanning which occurs along the melanin synthetic pathway. Tyrosinase activity increases when the skin is exposed to sunlight, thus triggering the cascade which causes the darkening of the skin. Despite an understanding of the enzymatic processes underlying melanin production, the precise mechanism by which the sun initiates this activity is still unknown.

The desire for a deep tan has generated a proliferation of products claiming to enhance the tanning process. Most of these products contain tyrosine, tyrosine derivatives and /or amino acid blends. Despite the claims of the producers, a number of independent studies have demonstrated that these products, when used according to package insert instructions, showed a lack of efficacy in tan acceleration.

Theophylline is a potent stimulator of melanogenesis in melanoma cell lines. This activity has been attributed to inhibition of mammalian phosphodiesterase which further causes an elevation in cAMP levels. cAMP is believed to increase the activity of tyrosinase. Consequently, it has also been postulated that melanin production can be increased by increasing cAMP levels. In support of this theory, a hormone, α-MSH, has been shown to increase melanin production through activation of adenylate cyclase, thereby increasing cAMP levels. Although this hormone can stimulate the tanning process, α-MSH is a potent neuropeptide and is unsuitable for use in topical creams.

What is needed in the art are new compositions which modulate melanin production and thereby lighten the skin or hair or promote tanning for both pharmaceutical and cosmetic purposes. The compositions should provide the modulation of melanin production by acting on specific receptors or enzymes in the melanin cascade. Surprisingly, the present invention provides such methods and compositions.

SUMMARY OF THE INVENTION

The present invention provides pharmaceutical and cosmetic compositions which are useful for modulating the production of melanin in the skin and in the hair. Certain compositions are useful in enhancing the tanning process by increasing skin pigmentation, while other compositions will be useful in reducing skin pigmentation to lighten skin color. The present invention further provides methods for modulating skin and hair color.

Thus, in one aspect, the present invention provides a composition for increasing melanin production in the skin or hair comprising a compound which is an adenosine-1 receptor antagonist, an adenosine-2 receptor agonist or a combination thereof, in a pharmaceutically acceptable lotion or cream.

In another aspect, the present invention provides a composition for decreasing melanin production in the skin or hair comprising a compound which is an adenosine-1 receptor agonist, an adenosine-2 receptor antagonist or a combination thereof, in a pharmaceutically acceptable lotion or cream.

In yet other aspects, the present invention provides methods of increasing or decreasing melanin production in a host. In these methods, an effective amount of one of the compositions above is administered to the host via topical application.

DETAILED DESCRIPTION OF THE INVENTION

Abbreviations

The following abbreviations are used herein: A1, adenosine-1; A2, adenosine-2; PMSF, phenylmethylsulfonylfluoride; α-MSH, α-melanin stimulating hormone; CPA, $N^6$-cyclopentyladenosine; CCPA, 2-chloro-$N^6$-cyclopentyladenosine; CHA, $N^6$-cyclohexyladenosine; CGS 22492, 2-((cyclohexylethyl)amino)adenosine; CGS 22989, 2-((cyclohexenylethyl)amino)adenosine; CHEA, 2-(2-cyclohexylethoxy)adenosine; CPT, 1,3-dimethyl-8-cyclopentylxanthine; CPX, 1,3-dipropyl-8-cyclopentylxanthine.

Compositions for the Modulation of Melanin Production

The present invention is a result of the surprising discovery that agonists and antagonists of the adenosine receptors are useful for the regulation of melanin production in human skin and hair. More particularly, adenosine-1 receptor antagonists and adenosine-2 receptor agonists have each been found to stimulate tyrosinase activity and subsequent melanin production. Conversely, adenosine-1 receptor agonists and adenosine-2 receptor antagonists inhibit tyrosinase activity and thereby decrease melanin production.

In view of the above surprising discovery, the present invention provides compositions which are useful for modulating melanin production in a host. The compositions comprise an adenosine-1 receptor agonist, an adenosine-1 receptor antagonist, an adenosine-2 receptor agonist, an adenosine-2 receptor antagonist, or combinations thereof in a topical carrier.

In one embodiment, the invention provides compositions for increasing melanin production in a host. These compositions comprise an adenosine-1 receptor antagonist, an adenosine-2 receptor agonist, or combinations thereof in a topical carrier.

Figure 1:
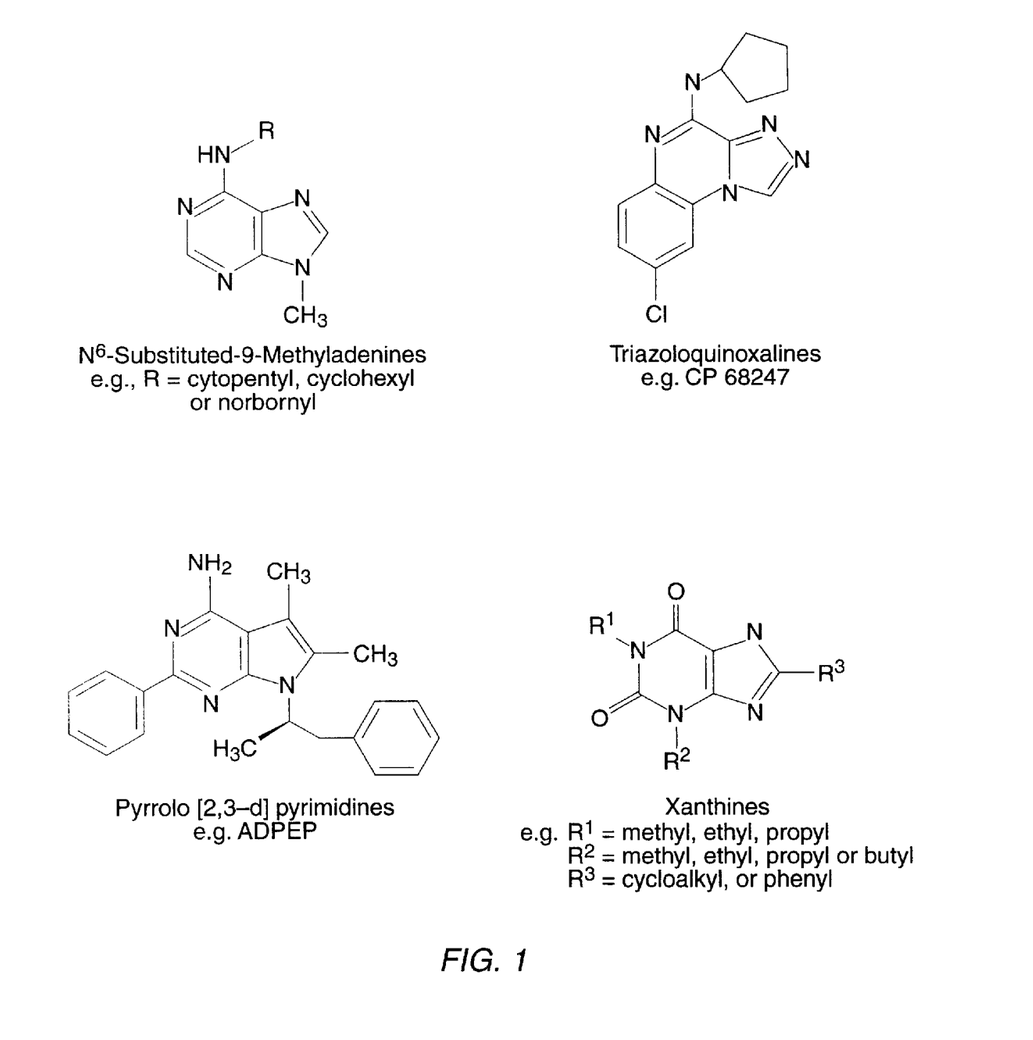
FIG. 1 provides the structures of some representative adenosine-1 receptor antagonists.

Adenosine-1 receptor antagonists which are useful in the present invention include a variety of bicyclic and tricyclic nitrogen heterocycles which can be considered analogs or derivatives of adenosine. The prototypic adenosine receptor antagonists were the xanthines, theophylline and caffeine. Recently, non-xanthine antagonists have been developed which are tricyclic and include triazoloquinazolines, triazoloquinoxalines and imidazoquinolines. Still other potent A1-selective antagonists are derived from 7-deazaadenines or other deazaadenines. As is apparent from the above noted group of compounds, antagonists which are active at the Al receptor will be flat, and aromatic or π-electron rich. See, Jacobsen, et al., *J. Med. Chem.* 35:407–422 (1992); Williams, et al., *Pharmacol. Biochem. Behav.* 29:433–441 (1988); and Brackett, et al., *Biochem. Pharmacol.* 47:801–814 (1994), the disclosures of each being incorporated herein by reference. Additionally, the ring systems associated with such activity often contain a fused 6:5 ring system. In general the presence of hydrophobic substituents such as alkyl (both saturated and unsaturated), cycloalkyl (saturated and unsaturated) and aryl groups will enhance the binding of the associated compound to the receptor (see FIG. 1 for representative structures). Examples of suitable heterocyclic systems include benzimidazoles, benzo[1,2 or 5,4-c]dipyrazoles, benzo[g]pteridine-2,4-diones, dibenz[b,f]azepines, imidazo[1,2-a]pyrazines, imidazo[4,5-b]pyridines, imidazo[4,5-c] quinolines, imidazo[4,5-f]quinazoline-7,9-diones, imidazo[4,5-g]quinazoline-6,8-diones, pteridine-2,4-diones, pyrazolo[3,4-b]pyridines, pyrazolo[3,4-d]pyrimidines, pyrazolo[4,3-d]pyrimidines, pyrazolo[4,3-c]quinolines, pyrimidines, pyrrolo[2,3-d]pyrimidines (7-deazaadenines), quinazolines, thiazolo[2,3-b]quinazolines, thiazolo[4,5-d]pyrimidine-5,7-diones, thiazolo[5,4-d]pyrimidine-5,7-diones, [1,2,4]triazolo[4,3-b]pyridazines, [1,2,4]triazolo[1,5-e]quinazolines, [1,2,4]triazolo[4,3-a]quinazolines, and xanthines.

In preferred embodiments, the adenosine-1 receptor antagonist is a CPT, CPX, ADPEP, a triazoloquinoxaline (e.g., CP 68247), an imidazoquinoline, a 7-deazapurine (e.g., 2-phenyl-7-deazaadenine), or a $N^6$-substituted-9-methyladenine (e.g., $\pm N^6$-endo-norbornyl-9-methyladenine and $N^6$-cyclopentyl-9-methyladenine).

Figure 2:
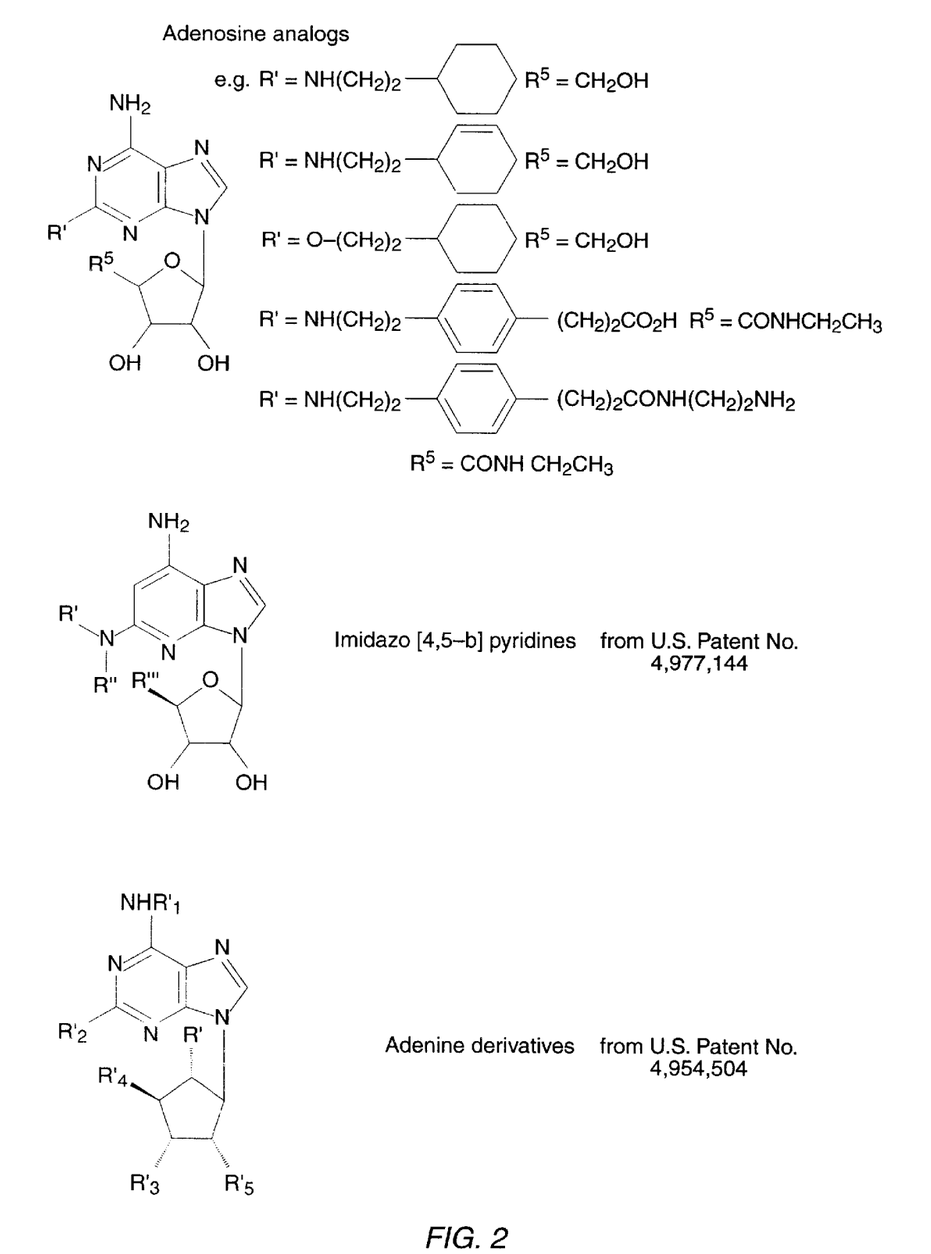
FIG. 2 provides the structures of some representative adenosine-2 receptor agonists.

Melanin production can also be increased with an adenosine-2 receptor agonist. In general, the adenosine-2 receptor agonist are similar in structure to the adenosine-1 receptor antagonists except that the agonist class are characterized as having an attached sugar, preferably a ribose, deoxyribose or analogs thereof which are known to those of skill in the art. A number of adenosine-2 receptor agonists have been described in U.S. Pat. Nos. 4,977,144, 4,954,504 and 5,206,222, the disclosures of which are incorporated herein by reference. In U.S. Pat. No. 4,977,144, the compounds are imidazo[4,5-b]pyridines having an amino group at the C5 position, a hydrogen, alkyl, aryl or arylalkyl substituent at the C6 position and an amino group at the C7 position which is optionally substituted with, for example, lower alkyl, alkenyl, carbocyclic or heterocyclic aryl. Additionally, the N3 position is substituted with a ribose or modified ribose moiety (including esterified derivatives). In U.S. Pat. No. 4,954,504, the compounds described are adenosine derivatives in which the ribose moiety is replaced with a hydroxylated cyclopentyl moiety (representative structures are provided in FIG. 2). Preferably, the A2 receptor agonists are CGS 22492, CGS 22989, CHEA, and CGS 21680.

The adenosine-1 receptor antagonists and adenosine-2 receptor agonists will typically have activity levels which can be measured in adenosine receptor assays as well as in assays for stimulation of tyrosinase. Preferably, the A1 antagonists which are useful in the present invention will exhibit a $K_i$ of 10 μM or less, preferably 0.1 μM or less and more preferably 10 nM or less in an A1 receptor binding assay (see, Daly, *J. Med. Chem.* 25(3):197–207 (1982)). The A2 agonists will similarly exhibit a $K_i$ of 10 μM or less, preferably 0.1 μM or less and more preferably 10 nM or less in an A2 receptor binding assay (see, Daly, ibid.).

In addition to the above levels of activity, the compounds used in the compositions and methods of the invention directed to increasing melanin production will stimulate tyrosinase activity in an assay as described in Example 1, below. The compounds will typically stimulate tyrosinase activity which is greater than the levels obtained with equivalent amounts of theophylline. Preferably the level of tyrosinase activity will be greater than that obtained with equivalent amounts of 8-cyclopentyl-1,3-dimethylxanthine. More preferably, tyrosinase activity will be greater than that achieved with equivalent amounts of $N^6$-cyclopentyl-9-methyladenine.

Preferably, the compounds used for increasing melanin production will also be selective for either activation of the A2 receptor or inactivation of the A1 receptor. As used herein, the term "selective" means that agonist activity at one receptor is at least 50-fold and preferably at least 100-fold more active than agonist activity at the other receptor. Similarly, antagonist activity is "selective" if binding at one receptor is provides a $K_i$ which is at least 50-fold, and preferably 100-fold lower than binding at the other receptor. For example, a compound exhibiting a $K_i$ of 1.0 μM for the Al receptor is selective for the A1 receptor if the compound exhibits a $K_i$ of at least 50 nM and preferably 100 nM for the A2 receptor.

Adenosine-2 (A-2) receptor binding properties, indicative of the adenosine-2 receptor agonist activity of the compounds of the invention can also be determined in vitro by determining their ability to inhibit the specific binding of $^3$H-5'-N-ethylcarboxamido-adenosine ($^3$H-NECA), e.g. essentially as described by Bruns et al., *Mol. Pharmacol.* 29:331–346 (1986), in striatal membrane preparations from corpus striatum of male Sprague-Dawley rats. The concentration of a particular compound required to displace the specific binding of 4 nM $^3$H-NECA is determined in the presence of 50 nM cyclopentyladenosine.

Adenosine 1 (A-1) receptor binding properties of the compounds of the invention indicative of adenosine-1-receptor agonist activity are determined, e.g., essentially according to Bruns et al., *Proc. Natl. Acad. Sci. U.S.A.* 77:5547 (1980), by determining their ability to inhibit the specific binding of $^3$H-cyclohexyladenosine ($^3$H-CHA) in rat brain membrane preparations from male Sprague-Dawley rats. The concentration of a particular compound required to displace the specific binding of 1 nM $^3$H-CHA is determined.

Selectivity for the adenosine-2 (A2) receptor can be ascertained by comparing the relative potency in the two adenosine receptor assays.

Figure 3:
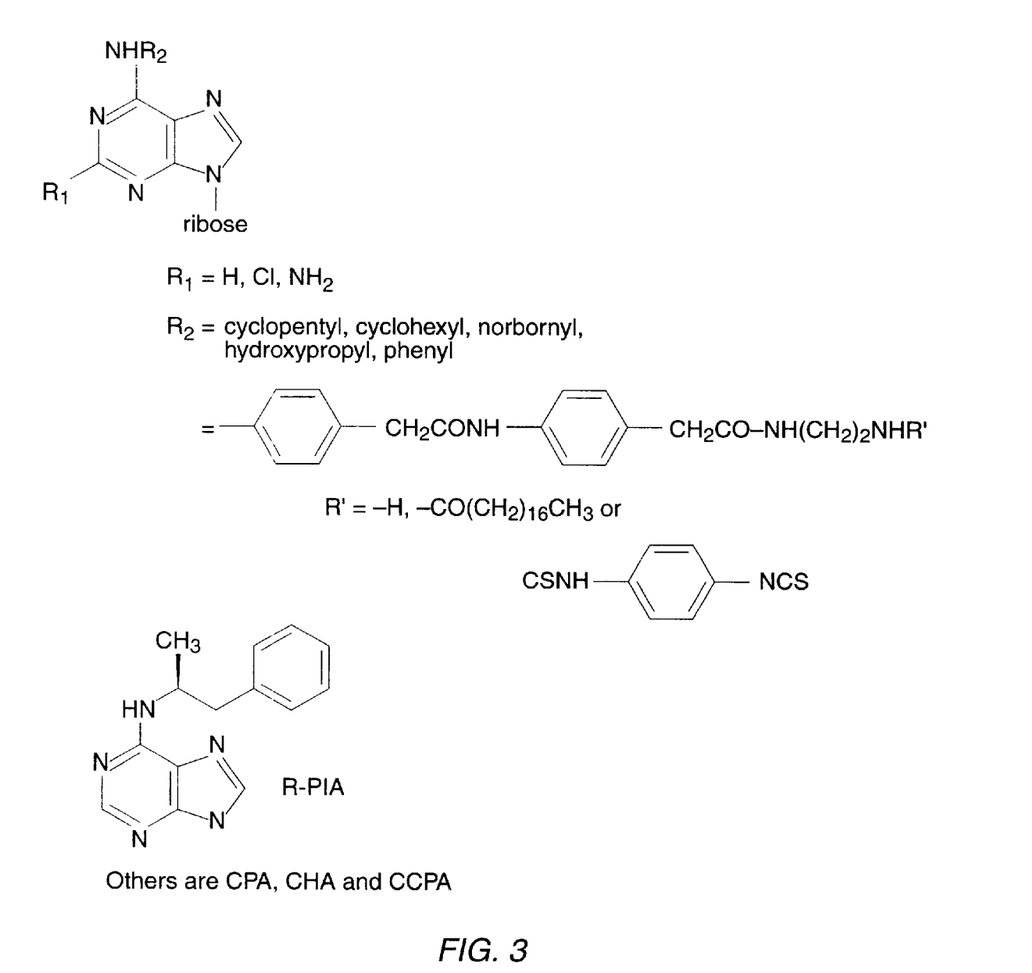
FIG. 3 provides the structures of some representative adenosine-1 receptor agonists.
Figure 4:
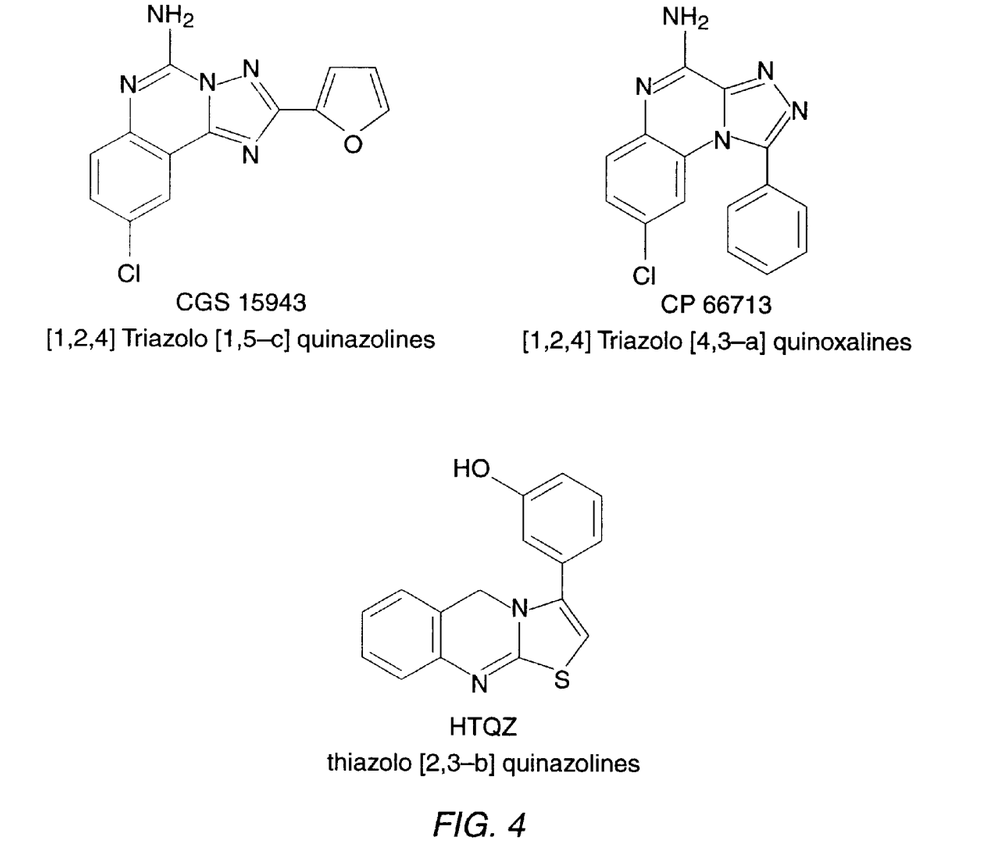
FIG. 4 provides the structures of some representative adenosine-2 receptor antagonists.

In another embodiment, the invention provides compositions for decreasing melanin production in a host. These compositions comprise an adenosine-1 receptor agonist, an adenosine-2 receptor antagonist, or combinations thereof in a topical carrier. As described above, certain compositions have been surprisingly found to stimulate tyrosinase activity, thereby increasing melanin production. The compounds present in those compositions are A1 receptor antagonists or A2 receptor agonists. Conversely, A1 receptor agonists (see FIG. 3) and A2 receptor antagonists (see FIG. 4) can be used to inhibit tyrosinase activity, thereby decreasing melanin production. Compounds which decrease melanin production can be used to decrease pigmentation in the skin and hair. Preferred compounds in the class of A1 receptor agonists are CPA, CHA, CCPA and R-PIA. Preferred compounds of the A2 receptor antagonist type are CGS 15943, CP 66713, HTQZ, 1-acetylene-3-methylxanthine, 5'-deoxy-5'-methylthioadenosine, 2-chloro-5'-deoxy-5'-methylthioadenosine, 5'-deoxy-5'-iodoadenosine, adenosine-5'-O-ethylcarbonate, and 5'-O-nitroadenosine.

The compounds described above can be prepared by general synthetic methods described in, for example, U.S. Pat. Nos. 4,954,504 and 4,977,144, previously incorporated by reference. Other compounds can be prepared by literature methods (see, for example, Jacobsen, et al., *J. Med. Chem.* 35:407–422 (1992) and references cited therein). Still other compounds can be obtained from suppliers such as Research Biochemicals Inc. (Natick, N.J., USA).

The compositions can be in a variety of forms, including for example, semi-solid and liquid dosage forms for either therapeutic or cosmetic use. Preferably the compositions are present as liquid solutions, suspensions, or creams. The preferred form depends on the intended mode of administration and application. See, for example, Flick E.W. COSMETIC AND TOILETRY FORMULATIONS, 2nd Ed., Noyes Publications, 1989.

While it is possible to administer the active ingredient alone, it is preferable to present it as part of a topical formulation. These formulations comprise the melanin modulating agent in an effective dose together with one or more pharmaceutically or therapeutically acceptable carriers and optionally other ingredients. Various considerations are described, e.g., in Gilman et al. (eds) (1990) GOODMAN AND GILMAN'S: THE PHARMACOLOGICAL BASES OF THERAPEUTICS, 8th Ed., Pergamon Press; NOVEL DRUG DELIVERY SYSTEMS, 2nd Ed., Norris (ed.) Marcel Dekker Inc. (1989), and REMINGTON'S PHARMACEUTICAL SCIENCES, the full disclosures of which are incorporated herein by reference.

Typically, the formulations will comprise a preparation for delivering a melanin modulating agent directly to the skin or hair comprising the modulating agent, typically in concentrations in the range from about 0.001% to 20%; preferably, from about 0.01 to about 10%; more preferably, from about 0.1 to about 5%; together with a non-toxic, pharmaceutically acceptable topical carrier. See DERMATOLOGICAL FORMULATIONS: PERCUTANEOUS ABSORPTION, Barry (ed.), Marcel Dekker Inc., (1983).

Topical preparations can be prepared by combining the melanin modulating agent with conventional pharmaceutical diluents and carriers commonly used in topical dry, liquid, cream and aerosol formulations. Typically, the preparation of suitable dosage forms (e.g., sprays, ointments, pastes, creams, lotions, gels, and solutions) will comprise mixing the active compound under sterile conditions with diluents and carriers along with any preservatives, buffers, or propellants which may be required.

Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like.

Drops may be formulated with an aqueous base or non-aqueous base also comprising one or more dispersing agents, suspending agents, solubilizing agents, and the like.

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

Methods for the Modulation of Melanin Production

The present invention further provides a method of modulating melanin production in a host by treating the host with an effective amount of an adenosine-1 receptor agonist, an adenosine-1 receptor antagonist, an adenosine-2 receptor agonist, an adenosine-2 receptor antagonist, or combinations thereof in a topical carrier.

The compositions which are useful in this aspect of the invention have been described in detail above, and particular Examples are provided below. The method of application will typically depend on the formulation used. For example, compositions which are developed to promote tanning, will be applied to the skin, in an effective amount to produce tanning, either by applying a solution or cream containing the active ingredient to the skin or by aerosol delivery of the compound to the area in which increased pigmentation is desired.

Similarly, compositions which are intended to lighten the pigmentation in the skin or hair can be topically applied to that area in which decreased pigmentation is desired. In view of the melanin modulating properties of the receptor agonists and antagonists described above, the present invention further provides methods for increasing the natural protection of the skin and hair against the effects of solar radiation or ultraviolet radiation. In particular, A1-receptor antagonists and A2-receptor agonists will be useful in cosmetically or pharmaceutically acceptable topical carriers for this aspect of the invention. Application of the compositions is as described above.

The foregoing description and the following examples are offered primarily for illustration and not as limitations. It will be readily apparent to those of ordinary skill in the art that the operating conditions, materials, procedural steps and other parameters of the compositions and methods described herein may be further modified or substituted in various ways without departing from the spirit and scope of the invention.

EXAMPLES

General

The compounds used in the Examples below were obtained from Irvine Scientific (Santa Anna, Calif., USA). $^3$H-Tyrosine and L-Dopa were obtained from Sigma Chemical Company (St. Louis, Miss., USA) All other reagents and solvents were of reagent grade or better and were obtained from commercial suppliers such as Aldrich Chemical Company (Milwaukee, Wis., USA).

EXAMPLE 1

This example illustrates a method for the determination of tyrosinase activation by compounds which are useful in the present invention.

Tyrosinase Activity Determination

Neonatal foreskins were obtained within two hours of elective circumcision. The foreskins were isolated and cleaned from fat tissue and cut into approximately 20 mg pieces.

The prepared skin (20 mg), phosphate buffer (250 µL, pH 6.8) containing phenylmethylsulfonylfluoride (PMSF), 20 µL of phosphate buffer (pH 6.8) containing 0.1% Triton X-100 and the test compound (activator or inhibitor) were added to a 2 mL polypropylene tube equipped with a scaled cap. The mixture was incubated for 2 hr in a water bath at 37° C. After the two hour period, the tubes were removed from the water bath and placed in a 2–8° C. ice bath. $^3$H-Tyrosine (10 µL) and L-Dopa (10 µL) were added and the tube was again incubated for an additional 4 hr in the water bath at 37° C.

The reaction was stopped by adding 1.0 mL of ice cold phosphate buffer followed by 0.5 mL of 10% charcoal in 0.1 M perchloric acid and mixed for 15 minutes. The mixture was centrifuged for 15 minutes at 10,000 rpm in an Eppendorf Centrifuge. After centrifugation, 0.5 mL of the supernatant was pipetted out and added to a scintillation vial containing 4.0 mL of scintillation fluid. The vial was placed in a scintillation counter and the counts were measured for 5 minutes. The tyrosinase activity was measured as $^3$H labeled release in cpm per hour per mg of skin.

Figure 5:
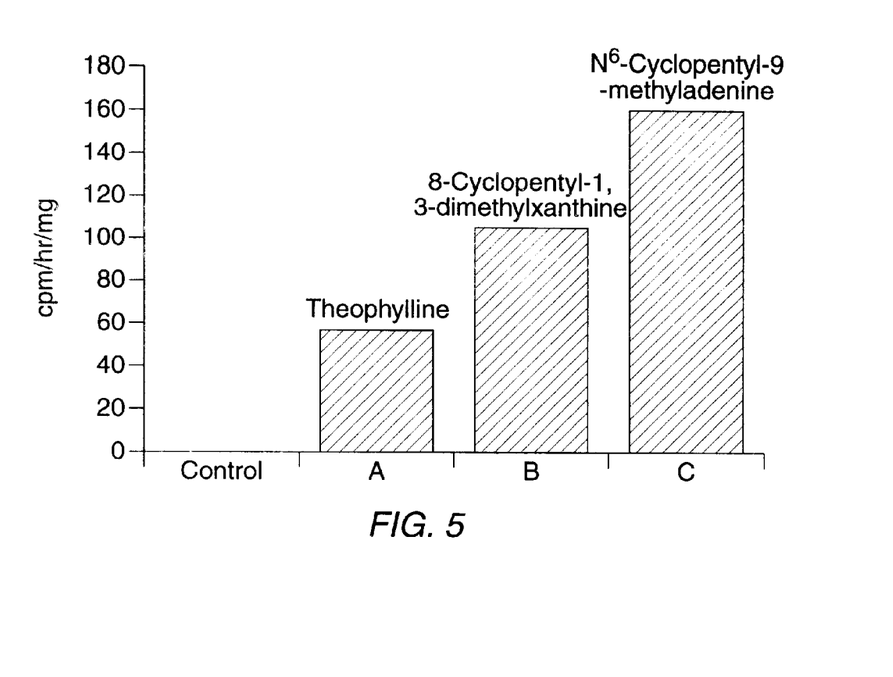
FIG. 5 is a bar graph which demonstrates tyrosinase stimulation for selected compounds of the invention.

The results of this assay are presented in FIG. 5 for theophylline, 8-cyclopentyl-1,3-dimethylxanthine and $N^6$-cyclopentyl-9-methyladenine.

EXAMPLE 2

This example provides one formulation which is suitable for the topical administration of an adenosine receptor agonist or antagonist.

A formulation for the topical delivery of 8-cyclopentyl-1,3-dimethylxanthine was prepared by first heating each of two phases to 75° C. and combining the two phases with high-shear mixing as follows: Phase I, containing by volume glyceryl stearate (3%), Steareth-21 (2.5%), cetyl alcohol (1.0%), PPG-15 Stearyl Ether (4.2%), cyclomethicone (1.8%), mineral oil (7.0%), almond oil (2.0%) and 8-cyclopentyl-1,3-dimethylxanthine (1.0%), was combined with Phase II containing by volume glycerol (4.0%), germaben 11 (1.0%) and demineralized water (to 100%). The resulting mixture was allowed to cool with moderate stirring and packaged in a suitable container.

EXAMPLE 3

This example provides a second formulation which is suitable for the topical administration of an adenosine receptor agonist/antagonist.

The adenine derivative and formulation components present in this example are all commercially available from Research Biochemical, Inc. (Natick, Mass., USA), Stepan Co. (Northfield, Ill., USA), Spectrum Quality Products, Inc. (Gardena Calif., USA) and B. F. Goodrich (Cleveland, Ohio, USA).

| Components | Weight % |
|---|---|
| Part A | |
| Isopropyl Isostearate | 4.00 |
| Isostearyl Isostearate | 6.00 |
| Acrylates/$C_{10-30}$ Alkyl Acrylate Crosspolymer | 0.20 |
| Carbomer 2984 | 0.20 |
| Part B | |
| $N^6$-Cyclopentyl-9-methyladenine | 0.50 |
| Mineral Oil | 19.50 |
| Polyglyceryl-3 Diisostearate | 1.00 |
| Part C | |
| Propylene glycol | 3.00 |
| Aminomethyl Propanol | 0.25 |
| Phenoxyethanol, Methyl Paraben, Ethyl Paraben, Propyl Paraben and Butyl Paraben (0.2% each) | 0.50 |
| Methylhydroxypropyl Cellulose | 0.10 |
| Deionized water q.s. | 100.00 |

The Carbomer 2984 and Acrylates/$C_{10-30}$ Alkyl Acrylate Crosspolymer are combined at room temperature with a mixture of isopropyl isostearate and isostearyl isostearate to form Part A.

Part C is prepared by first dispersing methylhydroxypropyl cellulose in 15% of the water. The remaining components of Part C are combined and added to the cellulose dispersion. The combined mixture is then heated to 65° C. Part A (20° C.) is added to Part C (65° C.) and the mixture in homogenized. Part B is then added and the emulsion is stirred for 45 minutes, then packaged in a suitable container.

EXAMPLE 4

This example illustrates the stimulation of melanin synthesis in cell culture using $N^6$-Cyclopentyl-9-methyladenine.

Materials:

A Mouse, Cloudman S91 Melanoma Cell line (Clone M-3, ATCC CCL-53.1) was used. The cells were flown as monolayers. These cells multiply 7–8 fold in 7 days and are know to produce melanin in over 50% of the cells up to at least 33 passages. Horse serum, fetal Bovine serum, Penicillin-streptomycin and F-10 nutrient mixture were all obtained from Life Technologies (GIBCO, Grand Island, N.Y.). $N^6$-Cyclopentyl-9-methyladenine (N-154) and C-102 (CPT) were obtained from RBI (Natick, Mass.). 1-Oleoyl-2-acetyl-rac-glycerol, activated charcoal, Triton X-100, phenyl methyl sulfonyl fluoride, theophylline, synthetic melanin and L-tyrosine-[Ring-3,5] were all obtained from Sigma Chemical Co. (St. Louis, Mo.). The culture medium used was Ham's F-10. The composition of the medium was as follows: Ham's F-10 Nutrient Mixture (82.5%), horse serum (15.0%), fetal bovine serum (2.5%), penecillin-streptomycin mixture (1.0%).

Procedure:

Cells were incubated with the indicated reagents (see FIG. 6) at 37° C. under 5% $CO_2$ atmosphere for 5–7 days. At the time of harvest, exhausted medium was removed from flasks/wells and cells were treated with 1–5 mL of 0.25% trypsin for 2–3 minutes. Cell suspension was transferred into a centrifuge tube containing equal amounts of Ham's F-10 medium and centrifuged at 1800 rpm for 3 minutes. After discarding the supernatant, cells were washed with 1–3 mL of phosphate buffered saline (PBS) and again re-suspended in PBS. An aliquot was used for cell counting by Trypan Blue exclusion method.

The extraction procedure was carried out on ice or at 4° C. Cell suspension was centrifuged to remove the supernatant. To the pellet was added 0.5 mL of lysis buffer (containing 1% Triton X-100, 0.1 mM phenylmethylsulfonyl fluoride, pH 6.8) and the mixture was vortexed. The tubes were left on ice for 15 minutes with occasional mixing, and then centrifuged at 15000 g (13,000 rpm) for 15 minutes. The supernatant was separated and the pellet was used for measuring the melanin content.

Figure 6:
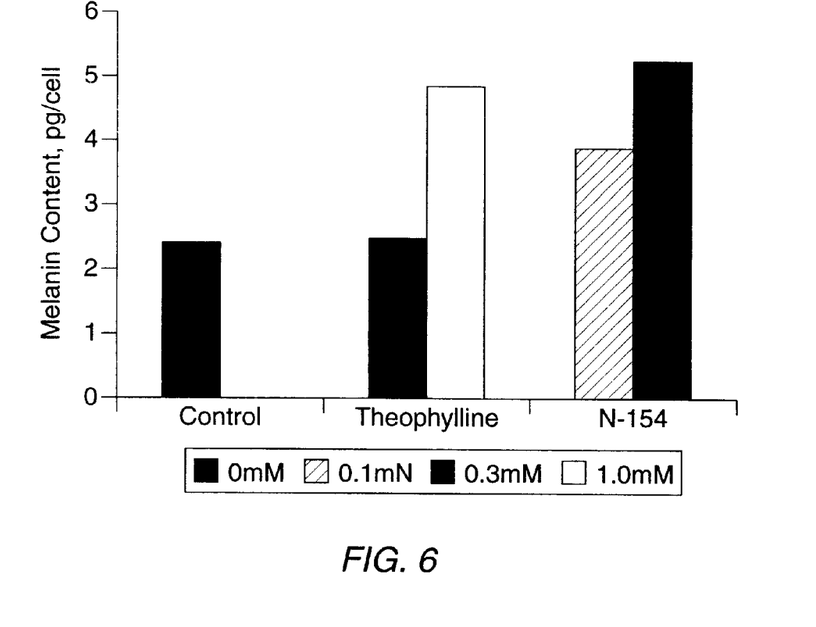
FIG. 6 is a bar graph which demonstrates stimulation of melanin synthesis by selected compounds of the invention.

The pellet (from above extraction) was dissolved in 0.25 mL of 0.5 N NaOH and the optical density was measured at 475 nm. The melanin content was determined from a standard curve obtained by using a synthetic melanin. The results are shown in FIG. 6.

All publications, patents and patent applications mentioned in this specification are herein incorporated by reference into the specification to the same extent as if each individual publication, patent or patent application was specifically and individually indicated to be incorporated herein by reference.

The foregoing is offered primarily for purposes of illustration. It will be readily apparent to those skilled in the art that the structures, methods, syntheses and experimental conditions, and other parameters of the system described herein may be further modified or substituted in various ways without departing from the spirit and scope of the invention.

What is claimed is:

1. A method of modulating melanin production in the skin or hair comprising applying to said skin or hair, an effective amount of a melanin production modulating agent selected from the group consisting of an adenosine-1 receptor antagonist, an adenosine-2 receptor agonist, an adenosine-1 receptor agonist, an adenosine-2 receptor antagonist and a combination of an adenosine-1 receptor antagonist and adenosine-2 receptor agonist or of an adenosine-1 receptor agonist and an adenosine-2 receptor antagonist, in a pharmaceutically acceptable lotion or cream.

2. A method in accordance with claim 1, wherein said modulation is an increase in melanin production and said compound is an adenosine-1 receptor antagonist.

3. A method in accordance with claim 2, wherein said adenosine-1 receptor antagonist is a triazoloquinoline.

4. A method in accordance with claim 2, wherein said adenosine-1 receptor antagonist is a triazoloquinoxaline.

5. A method in accordance with claim 4, wherein said triazoloquinoxaline has the structure

6. A method in accordance with claim 2, wherein said adenosine-1 receptor antagonist is an imidazoquinoline.

7. A method in accordance with claim 2, wherein said adenosine-1 receptor antagonist is a pyrrolo[2,3-d]pyrimidine.

8. A method in accordance with claim 7, wherein said pyrrolo[2,3-d]pyrimidine is 2-phenyl-7-deazaadenine.

9. A method in accordance with claim 2, wherein said adenosine-1 receptor antagonist is a $N^6$-substituted-9-menthyladenine.

10. A method in accordance with claim 9, wherein said $N^6$-substituted-9-methyladenine has the structure wherein R is cyclopentyl, cyclohexyl or norbornyl.

11. A method in accordance with claim 2, wherein said adenosine-1 receptor antagonist is a cycloalkylxanthine and phenylxanthine.

12. A method in accordance with claim 11, wherein said cycloalkylxanthine is a 1,3-dimethyl-8-cyclopentylxanthine or a 1,3-dipropyl-8-cyclopentylxanthine.

13. A method in accordance with claim 1, wherein said modulation is an increase in melanin production and said compound is an adenosine-2 receptor agonist.

14. A method in accordance with claim 13, wherein said adenosine-2 receptor agonist is a member selected from the group consisting of imidazo[4,5-b]pyridines, $N^9$-cyclopentyl-substituted adenine derivatives and 2-(p-(2-carboxyethyl)phenethylamino)-5'-N-ethylcarboxamidoadenosine.

15. A method in accordance with claim 13, wherein said adenosine-2 receptor agonist is a member selected from the group consisting of 2-((cyclohexylethyl)-amino)adenosine, 2-((cyclohexenylethyl)amino)adenosine, 2-((cyclohexylethoxy)adenosine, and 2-(carboxyethyl (phenylethyl)amino)adenosine.

16. A method in accordance with claim 1, wherein said modulation is a decrease in melanin production and said compound is an adenosine-1 receptor agonist.

17. A method in accordance with claim 16, wherein said adenosine-1 receptor agonist is a member selected from the group consisting of 1-deaza-2-chloro-N-cyclopentyladenosine, $N^6$-cyclopentyladenosine, $N^6$-cyclohexyladenosine, 2-chloro-$N^6$-cyclopentyladenosine and R-$N^6$-(2-phenyl-1-methylethyl) adenosine.

18. A method in accordance with claim 1, wherein said modulation is a decrease in melanin production and said compound is an adenosine-2 receptor antagonist.

19. A method in accordance with claim 18, wherein said adenosine-2 receptor antagonist is a member selected from the group consisting of 1-acetylene-3-methylxanthine, 5'-deoxy-5'-methylthioadenosine, 2-chloro-5'-deoxy-5'-methylthioadenosine, 5'-deoxy-5'-iodoadenosine, adenosine-5'-O-ethylcarbonate, and 5'-O-nitroadenosine.

20. A method in accordance with claim 18, wherein said adenosine- receptor antagonist is a member selected from the group consisting of 9-chloro-2-(2-furyl)--[1,2,4]triazolo-[1,5-c]quinazolin-5-amine, 4-amino-8-chloro-1-phenyl-[1,2,4]triazolo[4,3-a]quinoxaline, and 3-(3-hydroxyphenyl) 5H-thiazolo[2,3-b]quinazoline.

* * * * *